(12) United States Patent
Benje et al.

(10) Patent No.: US 7,182,840 B1
(45) Date of Patent: Feb. 27, 2007

(54) METHOD AND DEVICE FOR EXPLOITING HEAT RESULTING FROM THE PRODUCTION OF 1,2-DICHLOROETHANE

(75) Inventors: Michael Benje, Darmstadt (DE); Peter Porscha, Kelkheim (DE); Stefan Von Egelstein, Grossostheim (DE)

(73) Assignee: UHDE GmbH, Dortmund (DE)

( * ) Notice: Subject to any disclaimer, the term of this patent is extended or adjusted under 35 U.S.C. 154(b) by 0 days.

(21) Appl. No.: 10/129,344

(22) PCT Filed: Oct. 28, 2000

(86) PCT No.: PCT/EP00/10630

§ 371 (c)(1),
(2), (4) Date: Jul. 16, 2002

(87) PCT Pub. No.: WO01/34542

PCT Pub. Date: May 17, 2001

(30) Foreign Application Priority Data

Nov. 9, 1999 (DE) ................................ 199 53 762

(51) Int. Cl.
*B01D 3/28* (2006.01)
*C07C 17/383* (2006.01)

(52) U.S. Cl. ............................ 203/25; 203/27; 203/28; 203/72; 203/DIG. 8; 203/DIG. 9; 570/246; 570/262

(58) Field of Classification Search ................. 203/23, 203/25, 27, DIG. 8, DIG. 9, 72, 100, 28, 203/89; 570/216, 262, 252–254, 246
See application file for complete search history.

(56) References Cited

U.S. PATENT DOCUMENTS

| 3,963,584 A | * | 6/1976 | Tsao ............................. 203/49 |
|---|---|---|---|
| 4,257,850 A | * | 3/1981 | Rechmeier et al. ........... 203/29 |
| 4,347,391 A | | 8/1982 | Campbell |
| 4,351,976 A | * | 9/1982 | Ariki et al. .................. 570/262 |
| 4,419,301 A | * | 12/1983 | Nahra et al. ................. 261/118 |
| 4,672,142 A | | 6/1987 | Hundeck et al. |
| 4,747,914 A | * | 5/1988 | Schwarzmaier et al. ...... 203/22 |
| 4,774,372 A | | 9/1988 | Wachi et al. |
| 4,873,384 A | | 10/1989 | Wachi et al. |
| 6,235,953 B1 | | 5/2001 | Schwarzmaier et al. |
| 6,252,125 B1 | * | 6/2001 | Porscha ...................... 570/246 |

FOREIGN PATENT DOCUMENTS

| CA | 1204787 | * | 5/1986 |
|---|---|---|---|
| DE | 24 27 045 | | 1/1975 |

(Continued)

*Primary Examiner*—Virginia Manoharan
(74) *Attorney, Agent, or Firm*—Marshall & Melhorn, LLC

(57) ABSTRACT

The invention relates to a method and a device for the optimal use of reaction heat resulting from the production of 1,2-dichloroethane from ethene and chlorine. The aim of the invention is achieved by extracting reaction heat liberated during the reaction of chlorine with ethene and the reaction heat contained in 1,2-dichloroethane. Extraction of said reaction heat from the reaction chamber occurs using at least one part of gaseous 1,2-dichloroethane (latent heat) and at least one part of liquid 1,2-dichloroethane (feelable heat) removed from the reaction chamber. Said reaction heat is used to heat two fractioning columns in order to purify 1,2-dichloroethane of impurities having a boiling point higher than 1,2-dichloroethane.

5 Claims, 1 Drawing Sheet

FOREIGN PATENT DOCUMENTS

| | | |
|---|---|---|
| DE | 29 35 884 A1 | 4/1981 |
| DE | 36 04 968 A1 | 8/1986 |
| DE | 40 39 960 A1 | 9/1991 |
| DE | 40 29 314 A1 | 3/1992 |
| DE | 41 33 810 A1 | 4/1993 |
| DE | 196 41 562 A1 | 1/1998 |
| DE | 199 16 753 C1 | 7/2000 |
| EP | 0 026 349 B1 | 4/1981 |
| EP | 0 075 742 * | 9/1982 |
| EP | 0 075 742 B1 | 4/1983 |
| EP | 0131932 * | 1/1985 |
| EP | 0 681 563 B1 | 11/1995 |
| GB | 1 422 303 | 1/1976 |
| WO | WO 94/17019 | 8/1994 |

* cited by examiner

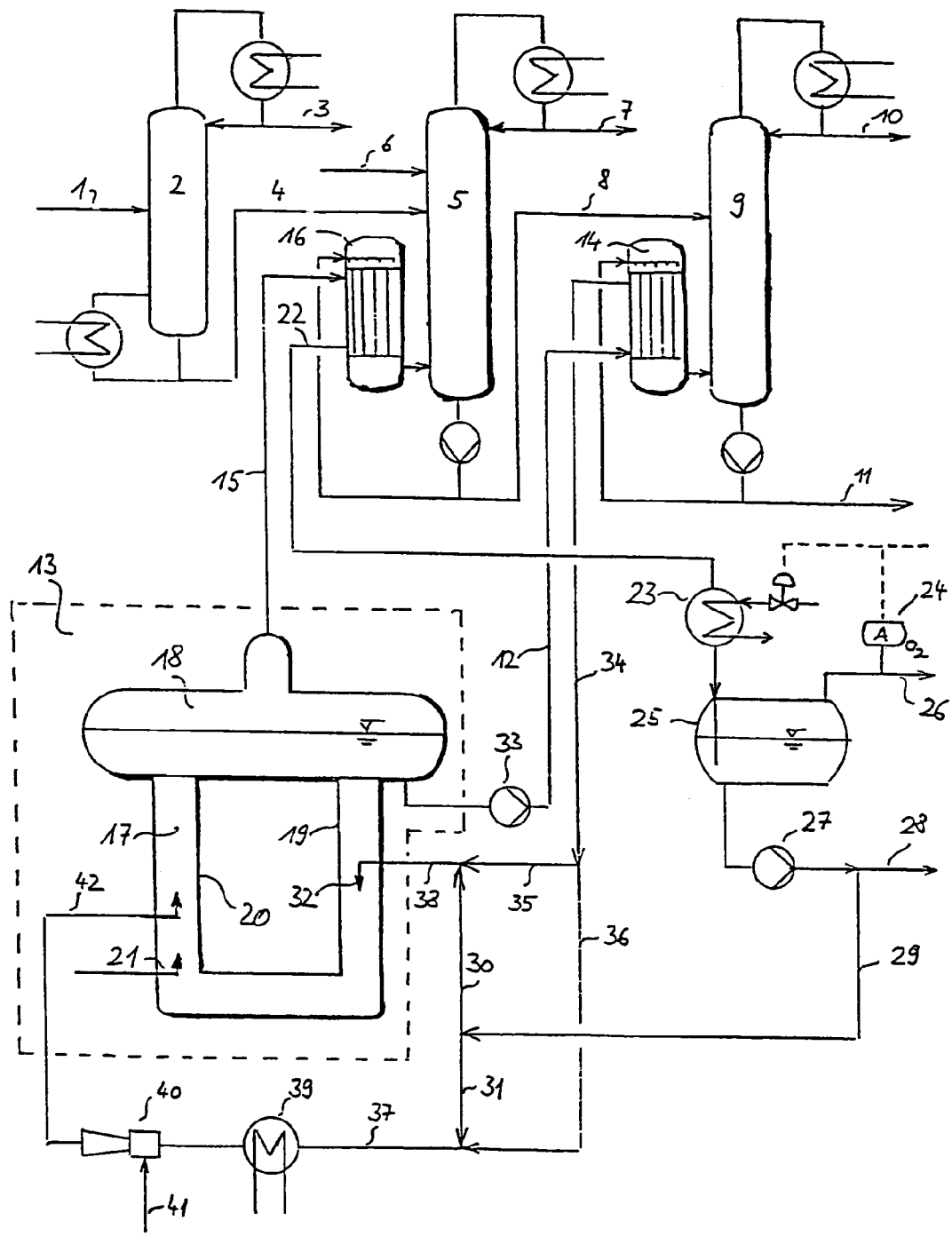

METHOD AND DEVICE FOR EXPLOITING HEAT RESULTING FROM THE PRODUCTION OF 1,2-DICHLOROETHANE

BACKGROUND OF THE INVENTION

The invention relates to a process for the production of 1,2 dichloroethane, hereinafter referred to as "EDC", which primarily serves as an intermediate product in the production of monomer vinyl chloride, hereinafter referred to as "VCM", which, in turn, is used to produce polyvinyl chloride (PVC), and the invention also relates to a facility for running the said process. Hydrogen chloride (HCl) is obtained when EDC is reacted to produce VCM. Hence, the preferred method of producing monomer vinyl chloride (VCM) from ethene $C_2H_4$ and chlorine $Cl_2$ such that a balance is maintained between the hydrogen chloride (HCl) produced and consumed in the various reactions, which is substantiated as follows:

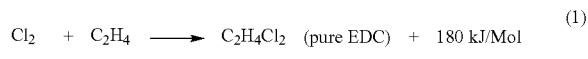
(1)

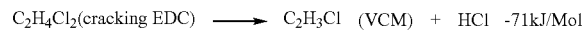
(2)

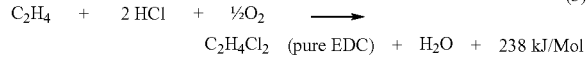
(3)

The process for the production of VCM with an adequate HCl balance—hereinafter referred to as "balanced VCM process"—comprises the following process steps:

a direct chlorination in which one portion of the required EDC is produced from ethene $C_2H_4$ and chlorine $Cl_2$ and made available as the so-called pure EDC, the recovery of the reaction heat developed in this direct chlorination being the main aim of the invention;

an oxichlorination in which the remaining portion of the required EDC is produced from ethene $C_2H_4$, hydrogen chloride HCl and oxygen $O_2$ and made available as the so-called raw EDC;

a fractionating EDC purification in which the secondary products formed in the oxychlorination and EDC pyrolysis sections are removed from the raw EDC and the recycle EDC returned from the fractionation section in order to obtain a so-called feed EDC suitable for use in the EDC pyrolysis section, the use of the reaction heat developed in the direct chlorination of the EDC distillation being the main aim of the invention;

an EDC pyrolysis in which the pure EDC is combined with the feed EDC and in which the EDC mixture called crackable EDC is then thermally cracked, the cracked gas obtained consisting of VCM, hydrogen chloride HCl and non-reacted EDC as well as by-products;

a VCM fractionation in which the desired pure VCM product is separated from the cracked gas while the other essential substances, viz. HCl and non-reacted EDC contained in the cracked gas are recoverd specifically and returned as recycle HCl or recycle EDC in the balanced VCM process.

The accompanying substances formed in the cracked gas during the EDC pyrolysis have a detrimental effect on the purity of the VCM product. Any VCM purification by removing the accompanying substances is a relatively expensive method. Hence, users of the balanced VCM process are working hard to reduce the costs incurred for the VCM purification in the fractionation. One of the considerations involved is to limit the types and quantities of unwanted accompanying substances in the EDC pyrolysis. This inevitably leads to the requirement that the content of impurities in the crackable EDC used for EDC pyrolysis should be as low as possible. The impurities contained in the crackable EDC partly form during the production of pure EDC and partly during the admixture of recycle EDC. Some of the impurities contained in the crackable EDC constitute precursors in the EDC pyrolysis and initiate the formation of additional accompanying substances in the cracked gas. The aim, therefore, is to minimise the amount of precursors penetrating via the crackable EDC into the EDC pyrolysis.

Since the realisation of the balanced VCM process concept many suggestions were submitted to avoid or remove the associated and detrimental by-products and/or the accompanying substances. It is known that part of the EDC required for the EDC pyrolysis is produced in the direct chlorination process by means of a reaction of ethene $C_2H_4$ with chlorine $Cl_2$ to obtain liquid EDC. A high cooling capacity is required to maintain the reaction temperature since the reaction is exothermic. The direct chlorination reaction takes place in a circulated stream of the reaction product EDC in the presence of a Lewis acid (in most cases: iron (III) chloride) and an inhibitor (in most cases: oxygen). The distinguishing feature of the known reaction systems is the way in which circulation is accomplished, i.e. there are systems with natural circulation and systems with forced circulation.

Such a system with natural circulation is for instance described in DE 24 27 045. In this case, the reactants enter at the lower end of the riser of a loop-type reactor with natural circulation. The reactor inventory starts boiling in the upper part of the riser and the vapourous reaction products are directly piped to the bottom of a rectification column for direct heating of the latter.

The EDC reaction fluid may also be conveyed in a forced circulation system. A typical example of such a process is for instance described in DE 40 29.314 A1. The chlorine is taken in by an injector-type jet-of-liquid gas compressor and part of the chlorine dissolves in the reaction fluid. A downstream conventional gas header serves to admix the ethene by way of large gas bubbles. The complete stream then flows through a static mixer so that large gas bubbles are dispersed in order to facilitate the dissolution and the associated reaction. This type of system precludes any boiling of the reactor inventory, the EDC produced being withdrawn in the gaseous phase by flash evaporation of a part stream of the EDC reaction fluid. The heat recovery is accomplished in this system by means of the sensible heat contained in the EDC reaction fluid as described, for example, in EP 0 075 742 B1. The circulated liquid EDC stream passes through one or several thermosiphon reboilers which deliver heat for the column bottom, thereby transferring sensible heat to the boiling contents of the column bottom.

Patent DE 4029 314 A1 describes a direct chlorination process in which the overall content of all chlorinated by-products in the EDC produced in the loop-type reactor by means of a NaFeCl$_4$ catalyst is below the value of 500 ppm. This EDC purity grade is normally appropriate for feeding the EDC to the pyrolysis unit without any intermediate purification step. Such a purity grade is of utmost importance to suppress, on the one hand, any side reaction which might cause fouling of the pyrolysis tubes and, on the other hand, to produce VCM of high purity. It is therefore necessary that the EDC left unreacted in the pyrolysis, the so-called recycle EDC and the so-called raw EDC leaving the oxychlorination be purified in a distillative EDC fractionation with high energy input prior to feeding them to the EDC pyrolysis. If the EDC impurity content is specified below 500 ppm it is also necessary to provide an additional distillative purification step for the pure EDC leaving the direct chlorination.

As a rule, all EDC streams are purified by way of distillation, hence the so-called EDC distillation. To achieve EDC purification the raw EDC from the oxychlorination and the non-reacted EDC from the EDC pyrolysis undergo purification in an EDC distillation with high energy input. If required, it is also possible to purify the pure EDC from the direct chlorination together with the raw EDC and the recycle EDC in the EDC distillation section. The EDC stream to be purified is first sent to a fractionation column, hereinafter referred to as "light ends column" to remove the water and light ends; the partly purified EDC which still contains heavy ends is withdrawn as bottom stream from the light ends column and piped to a fractionation column for the separation of heavy ends, hereinafter referred to as "heavy ends column". The light ends column may be replaced by a series of separate columns.

The non-reacted recycle EDC from the EDC pyrolysis also contains heavy ends and is consequently fed to the heavy ends column. All process streams fed to the high ends column undergo distillation therein. A first part stream of EDC vapours freed to a large extent from heavy ends is withdrawn from the head of the heavy ends column, flows through the heat exchanger in which the vapours condense so that pure liquid EDC is obtained. The heavy ends are concentrated in the heavy ends column bottom. It is possible to purify the bottom discharge stream of the heavy ends column more intensely by feeding said stream to a second heavy ends column referred to as "vacuum column". A second part stream of purified EDC vapours freed to a large extent from the heavy end is withdrawn from the head of the heavy ends column, flows through the heat exchanger in which the vapours condense so that pure liquid EDC is obtained. Upon being combined both streams form the crackable EDC. The bottom discharge stream from the vacuum column essentially consists of heavy ends and a small portion of EDC and must be disposed of.

Practical experience has shown that the direct chlorination reactor ranges among the largest consumers of coolant and the heavy ends column and vacuum column among the largest consumers of heating energy within an EDC/VCM plant operated by the balanced VCM process. On the basis of economic considerations, different concepts have been framed to reduce energy consumption, said concepts focusing on the heating of the columns. These concepts either make use of the reaction heat obtained in the direct chlorination for direct or indirect heating of the EDC distillation section or they only save comparably lower-valent heating energy by application of the rectification basics, including the compression of vapours and the distillative EDC purification. However, the process concepts suggested involve the disadvantages described in the following paragraphs.

As regards the direct heating method, the product vapours formed in the direct chlorination reactor are directly fed to the heavy ends column bottom as, for example, described in patents DE 29 35 884 and DE 24 27 045. The diameter of the high ends column and the surface area of its reflux condenser become very large because the multiple amount of EDC compared with the amount of EDC newly formed in the direct chlorination unit, will evaporate in the exothermal boiling reaction when no external cooling is provided and because they will need rectification in the heavy ends column in addition to the other EDC streams. As liquid EDC—also the multiple of the amount of the EDC newly formed in the direct chlorination reactor—must at the same time be returned from the bottom of the heavy-ends column to the reactor, the reactor will automatically reach an elevated level of higher-boiling by-products which, on the one hand, has a detrimental effect on the catalyst efficiency and, on the other hand, promotes the formation of by-products, finally resulting in a deteriorated yield.

On account of the process correlations described above, the reaction heat obtained in the direct chlorination unit is also unsuitable for the direct heating of the vacuum column of the EDC purification since the concentration of heavy ends in the bottom is 90% which exceeds the level prevailing in the heavy ends column.

There are two options for indirect heating: either liquid or vaporous EDC. The consequences involved are described in DE 196 41 562, DE 41 33 810 A1, DE 40 39 960 A1, DE 36 04 968 and EP 0 075 742 B1, details as follows:

If thermosiphon reboilers are used in the interconnected columns of the process stream system involved, adequate heating requires that an operational temperature difference of approx. 20 to 25° C. be ensured. The reaction temperature prevailing in the reactor must be raised considerably compared to the temperatures in the bottom of the columns involved in EDC purification in order to permit indirect reaction heat transfer to the thermosiphon reboilers. The required rise in temperature entails a deterioration of the EDC yield and an enhancement of by-product formation, and it will thus increase the amount of substances to be removed by distillation and the amount of heat required for the distillation.

The reaction heat developed in the reactor can also be transferred to heaters in the bottom of the interconnected EDC purification columns, even at relatively low reactions temperatures, provided that their operating pressure level is lowered to a value which, as a rule, is below the atmospheric pressure. This will inevitably lead to a larger diameter of the heavy-ends column and to a larger size of the reflux condenser which will have a detrimental effect on the process economy.

Patents EP 0 075 742 B1 and DE 41 33 810 A1 as well as this invention provide for the utilisation of liquid EDC from the direct chlorinations reactor but not for a use of the enthalpy of the vaporous EDC.

Patents DE 196 41 562 and DE 36 04 968 as well as this invention provide for the utilisation of the vaporous EDC and not of the liquid EDC.

OBJECT OF THE INVENTION

The aim of the invention therefore is to make optimum use of the heat released by the reaction enthalpy when applying the balanced VCM process.

SUMMARY OF THE INVENTION

The process of the type described above, which is the subject of this invention, permits to achieve the aim involved by providing for a removal of the reaction heat released in the reactor chamber by the reaction of chlorine with ethene and of the reaction heat contained in the 1,2-dichloroethane from said reaction chamber by at least one portion of vaporous 1,2-dichloroethane (latent heat) and at least another portion of liquid 1,2-dichloroethane (sensible heat) so that said heat can be exploited for heating two fractionation columns required to remove from the 1,2-dichloroethane any impurity which is heavier than the 1,2-dichloroethane.

An embodiment of the invention provides for the use of falling film evaporators as bottom heaters in the EDC distillation columns of the EDC purification unit, said evaporators being heated with the reaction heat from the direct chlorination. A special feature of the falling-film evaporators is that they can be operated at large temperature difference but theoretically also at any low temperature difference. In the falling film evaporator, the liquid and vapours to be heated flow in a co-current downwards in the vertical tube bundle on the tube side of the heat exchanger, whereby the liquid is sent down the inner tube wall as falling film and the vapours forming in the tube are carried off downwards in the core section of the tube cross-sectional area. It is of decisive importance for a trouble-free operation to wetten the heating surface of the inner tube evenly and adequately with film liquid. It was found that the separating effect improves at low heat flux densities to such an extent that a larger portion of the readily volatile components of a given heat flow changes into the vapour phase.

This is a substantial aspect especially for the operation of the vacuum column, as it reduces the EDC product portion which would be lost by the bottom discharge stream of the vacuum column. Another embodiment of the process according to the invention, therefore, provides for the use of heat to pre-concentrate and post-concentrate the bottom products obtained in the fraction columns, i.e. the impurities in the 1,2-dichloroethane which are higher boiling than the 1,2-dichloroethane itself. To achieve a mild reaction the direct chlorination reactor can in this case be operated as boiling reactor at an evaporation temperature of approx. 110° C., which becomes feasible for conventional heavy ends and vacuum columns on account of the falling film evaporators that are used.

A specific embodiment of the invention provides for an EDC part stream cooled by way of recovery of latent and sensible heat, said stream being returned to the reaction chamber and thus enhancing the flow in the reaction chamber.

Another embodiment of the invention provides for the dissolution of the chlorine to be used in the direct chlorination unit, the chlorine being dissolved in a small cooled bleed stream with the effect that a larger amount of chlorine can be dissolved in the EDC and that a smaller amount of EDC will be required to dissolve the chlorine. In this respect, the invention has the advantage that a major part of the heat contained in this EDC bleed stream can first be used to operate the EDC purification column, preferably for concentrating the heavy ends in the vacuum column, which will accordingly reduce the amount of coolant required to cool the bleed stream and to dissolve the chlorine.

Another advantage of this invention is that the split-up into several vaporous and liquid part streams at a non-fixed ratio will increase the range of freedom for the column controls and consequently remove certain restrictions for the control system.

Another embodiment of the invention provides for a further condensation in a secondary condenser, of the stream which is obtained as condensate by the recovery of the latent heat and which yet contains gaseous and vaporous components. During the secondary condensation of the EDC vapours, inert gas (within the meaning of reaction equation 1) and surplus ethene will not condense, part of the inert gas consisting of oxygen which is fed to the direct chlorination to inhibit side reactions of reaction (1) or which is entrained by the chlorine used and then removed together with vapours. An explosive mixture may form from the residual vaporous EDC and the surplus ethene owing to the constant rise in the partial pressure of the inert gas against the EDC during the condensation. A further embodiment of the invention therefore provides for the measurement of the oxygen content in the effluent gas. This measured variable is used to control the secondary condensation of the EDC in such a manner that no explosive mixture can form and that the largest possible amount of latent heat is removed from the gas/EDC/vapour mixture.

To achieve the aim of the invention provision is made for a facility suitable for the recovery of the reaction heat developed in the production of EDC from ethene and chlorine, said facility comprising a heavy ends column and a downstream vacuum column each of which is equipped with one falling-film evaporator, the evaporator assigned to the heavy ends column being heated with the EDC vapour from the direct chlorination reactor and that of the vacuum column being heated with liquid EDC from the said reactor.

For feeding gaseous chlorine into the direct chlorination reactor it is possible to provide at least one pipe for the EDC part stream in conjunction with a feed pipe to the injector for the intake of gaseous chlorine, and a pipe for feeding the chlorine-bearing EDC stream to the reaction section of the direct chlorination reactor.

To support natural circulation or to implement a forced circulation, the invention provides for an optional concept or for an embodiment that necessitate the installation of an EDC part stream pipe for feeding cooled EDC streams from the falling film evaporators so that the circulation velocity increases with the aid of a fine jet nozzle arranged in the downpipe of the direct chlorination reactor.

BRIEF DESCRIPTION OF THE DRAWINGS

The FIGURE shows a schematic flow chart of a facility in accordance with at least one embodiment of the present invention.

A typical layout of the process and the required facilities according to the invention is described on the basis of the flowsheet (FIGURE) and it illustrates the functions of the individual components, the process design being by no means restricted to the concept described hereafter.

DESCRIPTION OF THE PREFERRED EMBODIMENT

To achieve EDC purification the raw EDC from the oxychlorination and the non-reacted EDC from the EDC pyrolysis undergo purification in an EDC distillation with high energy input. If required, it is also possible to treat the pure EDC from the direct chlorination in the EDC distillation. The raw EDC 1 from the oxychlorination shown in the chart is first treated in light ends column 2 to separate the water from the light ends withdrawn via line 3 for light ends. The EDC obtained as bottom product in the light ends column still contains heavy ends and is fed to the heavy ends column 5 via line 4. The non-reacted recycle EDC from the EDC pyrolysis also contains heavy ends and is also fed to the heavy ends column 5 via line 6.

All process streams fed to the high ends column undergo fractionation therein. Purified EDC is withdrawn at the head of high ends column 5 via line 7 and obtained as pure EDC. The heavy ends are concentrated in the heavy ends column 5 bottom. The purification of the bottom product from high ends column 5 is enhanced by feeding the bottom product via line 8 to vacuum column 9. Purified EDC is withdrawn at the head of high ends column 9 via line 10 and obtained as pure EDC. The bottom discharge stream 11 from the vacuum column 9 essentially consists of heavy ends and a small portion of EDC.

Columns 5 and 9 are heated as follows: A liquid EDC stream is withdrawn from direct chlorination reactor 13 via line 12 and fed as heating agent to falling film evaporator 14 of vacuum column 9, said heating agent being subsequently removed again. The EDC vapour stream from direct chlorination reactor 13 is fed via vapours line 15 as heating agent to falling film evaporator 16 of high ends column 5. In falling film evaporators 14 and 16, the liquid to be heated flows downwards by gravity and as an evenly distributed film of boiling liquids from the head of the evaporator on the internal side of the heating tubes, part of said liquid thereby being evaporated.

A falling film evaporator in each process vessel unit permits a substantially larger surface area for heat transfer than that provided by conventional thermosiphon reboilers. This means that in the case of large plant capacities the bottoms of columns 5 and 9 can be heated with just one falling film evaporator, whereas several thermosiphon reboilers would be necessary.

The reaction that takes place in loop-type direct chlorination reactor 13 consisting of reaction section 17, stripping vessel 18, downpipe 19, riser 20, ethene injection point 21 and several feed points for liquid EDC, and the dissipation of the reaction heat will proceed as follows: Dissolved chlorine and dissolved ethene react in the liquid phase along reaction section 17 to form EDC part of which evaporates in stripping vessel 18.

EDC vapour is fed via vapours line 15 to falling film evaporator 16 required to heat high ends column 5. The major part of the EDC vapour condenses here. Outlet stream 22 from falling film evaporator 16 is fed to trimming condenser 23 required to control the system. It is imperative to make sure that oxygen, residual ethene and EDC vapour cannot form an explosive mixture during condensation. For this reason oxygen analyser 24 measures the oxygen content and the controller connected to this loop regulates the coolant flow rate to trimming condenser 23 but it is also possible to connect several controlling devices to said condenser.

Liquid EDC is then separated from non-condensable portions in feed vessel 25, the non-condensables being sent via effluent gas line 26 for further treatment. An EDC part stream is taken from feed vessel 25 by means of pump 27 and used as product stream for VCM production or, optionally, as EDC available for sale. The other EDC part stream 29 which has slightly cooled down by condensation is divided into EDC part streams 30 and 31. EDC part stream 30 is recycled to downpipe 19 of direct chlorination reactor 13 to support natural circulation by means of its pulse as free jet from nozzle 32 and also by its temperature which is lower than that of riser 20. Part stream 31 is exclusively used for dissolving chlorine.

An EDC stream is withdrawn from stripping vessel 18 by means of recycle pump 33 and sent to falling film evaporator 14 to heat vacuum column 9. EDC stream 34 cooled down upon the release of sensible heat is divided into EDC part streams 35 and 36. EDC part stream 35 is returned to downpipe 19 of direct chlorination reactor 13 to support natural circulation by means of its pulse as free jet from nozzle 32 and also by its temperature which is lower than that of riser 20.

The other EDC part stream 36 is exclusively used for dissolving chlorine. In this concept it is possible to combine both EDC part streams 31 and 36 as EDC stream 37 and EDC part streams 30 and 35 as EDC stream 38 as depicted in the FIGURE.

EDC part streams 31 and 36 are combined as EDC stream 37 and fed to EDC cooler 39 in which the EDC is further cooled, the more readily soluble gas component chlorine 41 being then taken in by injector 40 and dissolved. The chlorine-laden EDC stream 42 is then fed to reaction section 17.

The following example based on a computerised simulation serves to illustrate the concept: 4765 kg/h of ethylene (170 kmol/h) react with an equimolar amount of chlorine in loop-type direct chlorination reactor 13. The temperature in stripping vessel 18 is 110° C., the pressure is 2.1 bars (abs.). The amount of 70,465 kg/h of EDC vapours is fed via vapours line 15 to falling film evaporator 16 which delivers a heat of 5,094 kW to heavy ends column 5. The bottom temperature of heavy ends column 5 is 100° C., the residual amount of EDC condensing with the cooling water in trimming condenser 23, thus supplying 951 kW of heat.

The outlet stream from the condensation section has a temperature of 102° C. and is collected in feed vessel 25. The EDC laden effluent stream 26 of 2,848 kg/h is separated in said vessel. Pump 27 serves two functions: It transfers EDC part stream 28 of 14,017 kg/h to the next step for further treatment. It is also used to convey EDC part stream 29 of 53,600 kg/h, which in this case is identical with EDC part stream 30, to downpipe 19 of the loop-type reactor.

An EDC stream 12 of 250,000 kg/h is withdrawn from stripping vessel 18 by means of pump 33 and sent to falling film evaporator 14 in order to heat vacuum column 9. Falling film evaporator 14 supplies 1,814 kW of heat to vacuum column 9 the bottom temperature of which is 87 C. The cooled EDC stream 34 has a temperature of 92° C. at the outlet of falling film evaporator 14.

A 40% portion of said stream is diverted as EDC. part stream 35 and also returned to downpipe 19 of direct chlorination reactor 13. The remaining 60% portion (150,000 kg/h) is sent as EDC stream 37, which in this case corresponds to EDC part stream 36, to cooler 39 and cooled to 45° C. and then it takes up a rate of 12,100 kg/h chlorine in injector 40. A considerable amount of heat of the chlorine solution will again increase the temperature of EDC stream 41 to 75° C. Said stream is fed to reaction section 17 in which a nozzle system that enhances the flow should be installed

The invention claimed is:

1. Process for the recovery of reaction heat developed in the production of 1,2-dichloroethane from ethane and chlorine, comprising reacting chlorine and ethane in a reaction chamber thereby releasing heat and recovering the reaction heat contained in the 1,2-dichloroethane from the reaction chamber by means of at least one portion of vaporous 1,2-dichloroethane as latent heat and at least one more portion of liquid 1,2-dichloroethane as sensible heat so that said reaction heat can be exploited, solely for indirect heat transfer, for heating two fractionation columns required to remove from the 1,2-dichloroethane any impurity which is higher boiling than the 1,2-dichloroethane itself by pre-concentrating and post-concentrating the bottom products obtained in the fractionation columns, which bottom products comprise impurities in the 1,2-dichloroethane which are higher boiling than the 1,2-dichloroethane itself.

2. A process according to claim 1, wherein falling film evaporators are further deployed to heat the two fractionation columns used for removing impurities from 1,2-dichloroethane, said impurities being higher boiling than 1,2-dichloroethane.

3. A process according to claim 1, wherein at least one part stream of 1,2-dichloroethane condensed by the recovery of latent heat is recirculated to the reaction chamber to promote flow inside the reaction chamber.

4. A process according to claim 1, wherein at least one part stream of 1,2-dichloroethane condensed by the recovery of sensible heat is recirculated to the reaction chamber to promote flow inside the reaction chamber.

5. A process according to claim 1, wherein a part stream of 1,2-dicholoroethane cooled by the recovery of the latent and sensible heat is further cooled and then used to dissolve chlorine, the resulting solution being passed to the reaction chamber.

* * * * *